United States Patent [19]

Mier

[11] 4,300,883
[45] Nov. 17, 1981

[54] ORTHODONIC MODEL TRIMMER AID

[76] Inventor: John A. Mier, 3166 Palm Dr. #58, Fullerton, Calif. 92632

[21] Appl. No.: 142,774

[22] Filed: Apr. 22, 1980

Related U.S. Application Data

[63] Continuation of Ser. No. 965,837, Dec. 4, 1978, abandoned.

[51] Int. Cl.³ .............................................. A61C 19/00
[52] U.S. Cl. .......................................... 433/49; 269/57
[58] Field of Search ....................... 433/49; 269/57, 69, 269/73, 208, 304

[56] References Cited

U.S. PATENT DOCUMENTS

| | | | |
|---|---|---|---|
| 3,273,879 | 9/1966 | Floren | 269/73 |
| 3,367,224 | 2/1968 | Thiel | 269/57 |
| 3,554,244 | 1/1971 | Biscardi | 269/57 |
| 3,808,750 | 5/1974 | Mann | 433/25 |

FOREIGN PATENT DOCUMENTS

| | | | |
|---|---|---|---|
| 2534378 | 2/1977 | Fed. Rep. of Germany | 433/49 |
| 42916 | 6/1915 | Sweden | 433/49 |
| 371672 | 4/1932 | United Kingdom | 433/49 |

Primary Examiner—Gene Mancene
Assistant Examiner—John J. Wilson

[57] ABSTRACT

An Orthodonic model trimmer aid is provided which consists of a work table comprising a trough portion in which is placed a sliding plate which houses a sliding angulating holder comprising a hinge and a tapered locking pin. The locking pin is placed into selected holes on an angulating fence at desired angles. A surface portion of the fence can be set at varying angles depending on the desired angle for cutting of the dental model utilizing a typical dental trimming machine.

4 Claims, 9 Drawing Figures

4,300,883

ORTHODONIC MODEL TRIMMER AID

BACKGROUND OF THE INVENTION

This Application is a continuation of my Application, Ser. No. 965,837, filed Dec. 4, 1978, now abandoned.

This invention relates generally to dental model trimming machines and more particularly to a novel angulator device used in conjunction with a dental model trimmer.

Dental model trimmers are well known in the art. Such are utilized to prepare cast plaster models for a particular patient. As is known, the models are used as a tool for the doctor when providing study models, braces or the like. To prepare the models, part of the rough cast, usually provided in cubicle form, is trimmed away to articulate the occlusion of the teeth. This operation is performed on a grinding machine typically known in the art as a dental model trimming machine. It includes an abrasive wheel or other such device to grind down the rough cast. The cast is placed against the wheel utilizing a plate. The abrasive wheel wears down the model at the desired angle and provides the desired shape.

One problem in the art is the providing of a device to place the rough cast against the grinder at the desired angle. Many operators have to hold the cast by hand at an angle which results in a rough and difficult operation.

Accordingly, one object of this invention is to provide a device which can set a rough dental model cast at a desired angle against the grinder of a trimmer. Another object of the invention is to provide an angulator for a dental model trimmer which can easily be adapted to place the dental model cast at selected and desired angles against the grinding wheel. Other objects of the invention will be apparent from the detailed description.

DESCRIPTION OF THE INVENTION

Figure 1:
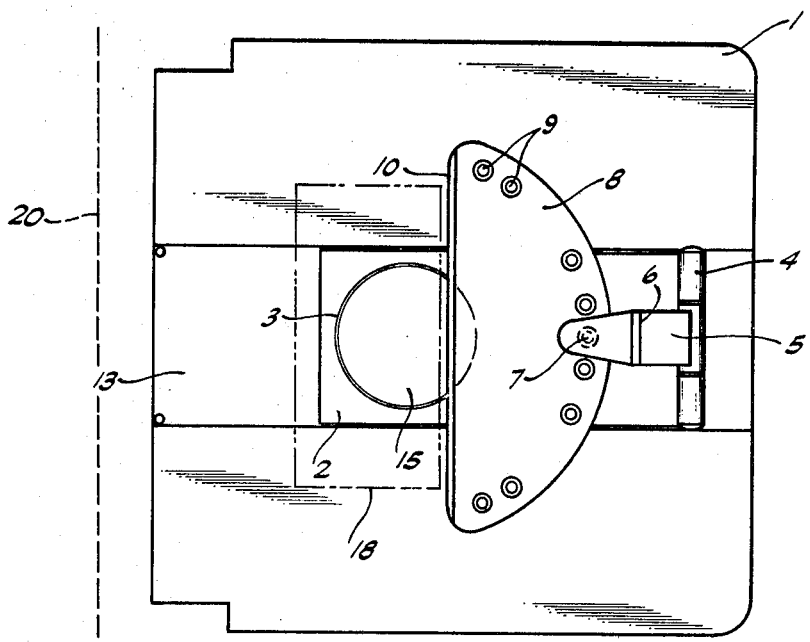
FIG. 1 shows a top view of the invention with the angulating fence 8 in a position parallel to the grinding wheel 20.

Referring to FIG. 1, there is provided an orthodonic work table or base 1. The grinding wheel fact 20 is shown and is connected to a standard grinding machine, not shown. The base may be housed within a table or other support device. The work table contains a trough portion 13 for placement of a sliding angulator holer 2. The holder comprises a hole or circular open portion 3. The sliding angulator holder 2 slides perpenticularly to wheel 15 within trough 13 of the base 1. An angulating fence 8 is provided which can be placed on or attached to the sliding holder 2. The fence contains a vertical portion 10 and a multitude, i.e. 4–15, perferably 8–13, holes which are tapered to receive the tapered locking pin 7. The angulating fence itself contains and is attached to a circular plate 15, shown in FIG. 4, which inserts within the open circular portion 3 of holder 2. The circular plate 15 attached to the fence 8, when inserted in the open portion 3 allows the fence to rotate and be rotated within the holder 2 and thus provides a pivot for the fence 8. As stated, the fence is semi-circular in form. The vertical portion 10 serves to contain the dental model which is placed on the base 1 against the vertical portion 10, one surface communicating with the vertical portion 10 on the opposite side of the circular portion 8 which contains the tapered holes 9. Thus, one side is against the grinding wheel 20 and one side is against portion 10.

Figure 2:
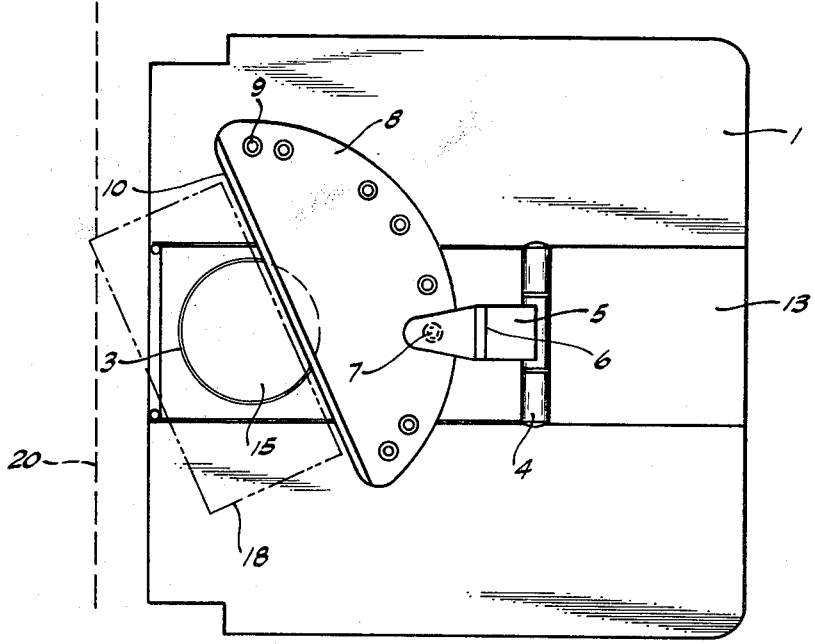
FIG. 2 shows a top view of the invention with the fence at an angle to the grinding wheel 20.

FIG. 2 shows a top view of the device except that the angulating fence is shown set at an angle. Thus, the model (dotted lines) is also at an angle against the wheel 20. As shown, the circular plate 15 is inserted within the hole portion 3 and thus serves as a pivot to rotate the angulating fence. The typical cast model 18 is shown in dotted lines. As is illustrated, the corner of the model can be cut off by placement of the model against the angulating fence at the desired angle with the corner or portion to be cut placed against the rotating grinding wheel. The grinding wheel grinds off the corner of the block 18. As is obvious, the angle which the angulator is set in reference to the sliding holder determines the angle of the model which is cut off by the grinding wheel 20.

Attached to or placed on to the grinding angulating holder 2 is a hinging arm 4 containing a tapered locking pin 7. The tapered locking pin 7 is inserted within one desired hole of the angulating fence. The hinging arm is connected to the sliding holder 2. Thus, the cast communicates with the vertical portion 10 of the fence which in turn communicates with the hinging arm 5 through pin 7 so that lateral movement of the holder places the model at the desired angle to the grinding wheel 20.

Figure 3:
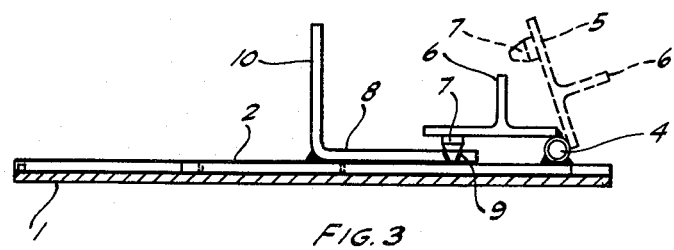
FIG. 3 shows a side view of the angulating fence.

FIG. 3 is a side view of the angulating fence and locking pin. As shown, the angulating fence rests on holder 2. There is a vertical portion 10 to the base 8. The holes 9 are within the base portion of the fence 8 such that the pin 7 can be inserted in such holes. There is a hinge 4 communicating with or attached to the hinging arm 5. The hinging arm 5 contains a vertical portion 6 and also the tapered locking pin 7. It can be seen from FIG. 3 that the inge 4 is utilized to rotate hinging arm 5 for placement of the pin into hole 9. Utilizing plate 15 inserted in portion 3, the angulating fence can be rotated at the desired angle and the locking pin placed within such holes for proper angulation of the slinding angulating holder. The case rests against vertical portion 10 and on tope of the holder 2.

Figure 4:
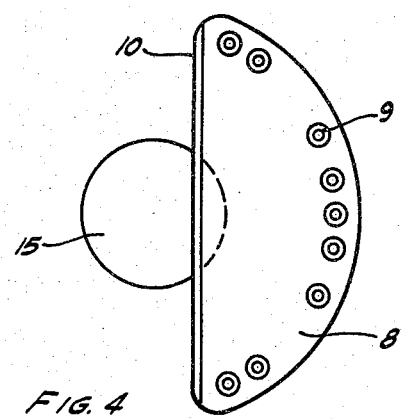
FIG. 4 shows a top view of the angulating fence on top of a solid circular plate 15 attached to the fence.

FIG. 4 shows a top view of the angulating fence. There are shown a multitude of holdes, i.e. 4–15, preferably 8–13. The number of holes shown is 9 and can be any number as determined by the operator depending on how many separate angles the operator desires. For example, the number could be anywhere from 2 to 100. Attached to the fence is the solid plate 15 which is inserted in the circular open portions 3 of the holder.

Figure 5:
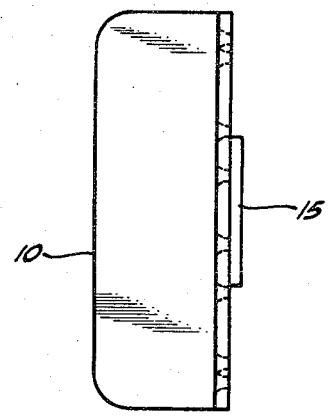
FIG. 5 shows a front view of the fence and connected circular plate 15.

FIG. 5 shows a front view of the fence illustrating the open portion 10 and the solid plate 15.

Figure 6:
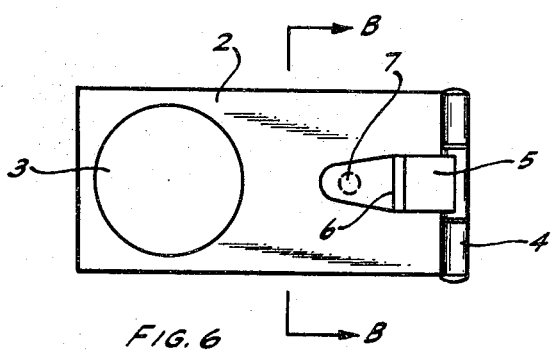
FIG. 6 is a top view of the sliding holder with circular open portion 3.

FIG. 6 shows a top view of the sliding angulating holder. Open circular portion 3 is shown within the plate 2. Also shown attached to plate 2 is the hinge 4, hinging arm 6 and tapered pin 7.

Figure 7:
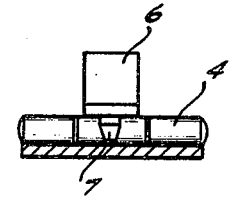
FIG. 7 is a front view of the sliding holder and angulating pin.

FIG. 7 is a front view of the hinging arm showing the hinge 4, hinging arm 6 and locking pin 7.

Figure 8:
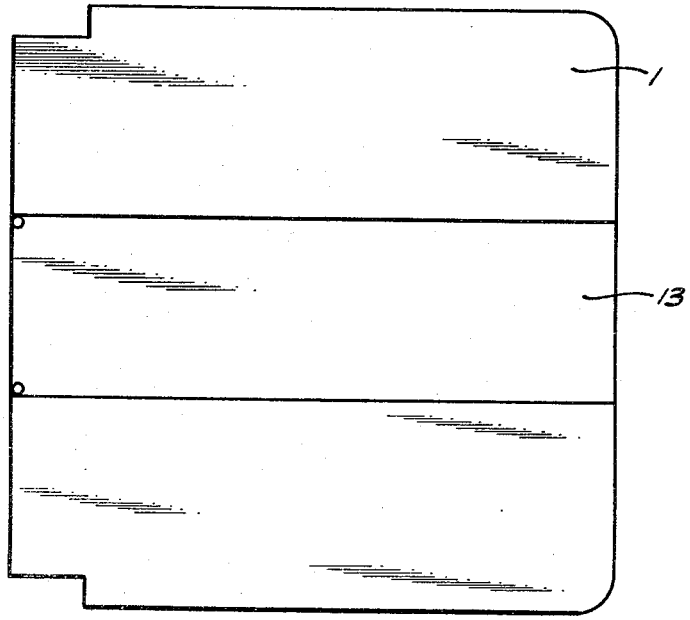
FIG. 8 is a top view of the base.

FIG. 8 simply shows the base plate 1 with the trough 13.

Figure 9:
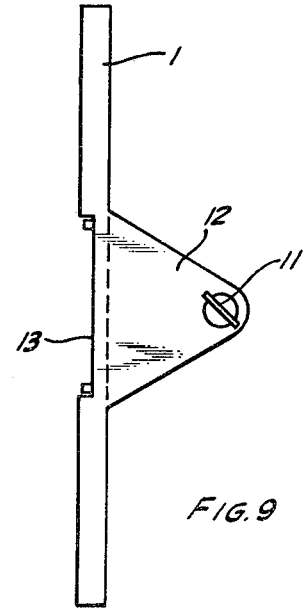
FIG. 9 is a front view of the tapered locking pin and hinge in operation.

FIG. 9 shows the base 1 with trough 13 and portion 12 and 11 for attachment of the base plate to any working table.

In operation, the user places the cast onto the table or base 1 and against the vertical portion 10 of the fence. The fence, with its circular plate 15 placed within the circular portion 3 is rotated to the desired angle. The locking pin 7 is placed within the desired hole 9 of the fence 8. At this stage of the operation, the sliding holder and angulating fence are in the proper position. The operator then pushes the angulating fence against which is placed the cast, and the cast is then placed against the rotating grinding wheel 20. The grinding wheel grinds down the case to the desired angle.

After some cutting action, the user can reset the angle as described above for cutting of a different portion of the model block 18.

It can be seen from the foregoing description that the device of this invention provides an easy method by which a user can rotate a dental model against a grinding wheel and provides a stable method of holding the model during the grinding operation.

I claim:

1. An angulating device for an orthodonic model trimmer comprising:
    (a) A base comprising a lateral trough portion;
    (b) A sliding angulating holder to which is attached an arm and said holder being positioned within said trough portion of said base;
    (c) An angulating fence containing a vertical portion adapted for placement onto said sliding angulating holder;
    (d) A plate attached to a flat portion of said fence; an opening within said holder for placement of said plate;
    (e) Means for locking said arm and said angulating fence in a multitude of angular positions;
    (f) Means whereby a dental cast can be placed onto said device for the trimming of said model.

2. The device of claim 1 containing a tapered locking pin attached to said (hinging) arm.

3. The device of claim 1 containing a circular plate attached to a flat portion of said fence and a circular opening within said holder for placement of said circular plate.

4. An angulating device for an orthodontic model trimmer comprising:
    (a) A base comprising a lateral trough portion;
    (b) A sliding angulating holder to which is attached an arm and said holder being positioned within said trough portion of said base;
    (c) A locking pin communicating with said arm;
    (d) An angulating fence containing a multitude of holes and containing a vertical portion adapted for placement onto said sliding angulating holder, said holes adapted for placement of said locking pin;
    (e) A circular plate attached to a flat portion of said fence; a circular opening within said holder for placement of said circular plate;
    (f) Means whereby a dental cast can be placed onto said device for the trimming of said model.

* * * * *